United States Patent [19]

Sharpe et al.

[11] 4,247,644

[45] Jan. 27, 1981

[54] **FOAM FLOTATION PROCESS FOR SEPARATING *BACILLUS THURINGIENSIS* SPORULTION PRODUCTS**

[75] Inventors: Eugene S. Sharpe, Eureka; Alberta I. Herman, Peoria, both of Ill.; Susanne C. Toolan, New Brunswick, N.J.

[73] Assignee: The United States of America as represented by the Secretary of Agriculture, Washington, D.C.

[21] Appl. No.: 64,678

[22] Filed: Aug. 8, 1979

[51] Int. Cl.$^3$ .............................................. C12N 3/00
[52] U.S. Cl. ...................................... 435/242; 435/832
[58] Field of Search ............... 435/242, 170, 246, 253, 435/822, 832

[56] References Cited

U.S. PATENT DOCUMENTS

| | | | |
|---|---|---|---|
| 3,075,887 | 1/1963 | Silliker et al. | 435/246 |
| 3,087,865 | 4/1963 | Drake et al. | 435/242 X |

OTHER PUBLICATIONS

Truskov "Isolating Pure Inclusion Produced in Cultures of *Bacillus Thuringiensis*", Cited in Chemical Abstracts, vol. 72 (1970), Abstract No. 77484e.

Kirk-Othmer, "Encyclopedia of Chemical Technology", Interscience Publishers, vol. 9, Second Edition, 1969, pp. 884 and 893–896.

Angus, "Separation of Bacterial Spores & Parasporal Bodies with a Fluorocarbon", J. Insect. Path., vol. 1, pp. 97-98 (1959).

Bateson, "Isolation of Crystalline Parasporal Bodies of *Bacillus thuringiensis*", Nature, vol. 205 (1965), pp. 622-623.

Pendelton, "Separation of the Spores & Crystals of *B. thuringiensis*", Nature, vol. 212 (1966), pp. 180-184.

Gingrich", "Flotation Procedure for Producing Spore Free Crystals", J. Invertebr. Path, vol. 10, (1968), pp. 180-184).

Fast., "The S-Endotoxin of *B. thuringiensis* III Rapid Method for Separating Parasporal Bodies from Spores", J. Inverteb Path, vol. 20 (1972), pp. 139-140.

Sharpe et al., "Separation of Spores & Parasporal Crystals of *B. thuringiensis* in Gradients of Certain X-ray Contrast agents", Appl. Environ. Microbiol., vol. 30 (1975), pp. 1052-1053.

Milore et al., "*B. thuringiensis* S. Endotoxin: Improved Technique for Separating Crystals from Spores", J. Invertebr. Path, vol. 29 (1977), pp. 230-231.

*Primary Examiner*—R. B. Penland
*Attorney, Agent, or Firm*—M. Howard Silverstein; David G. McConnell; Curtis P. Ribando

[57] ABSTRACT

Crystal-enriched suspensions are derived from sporulated cultures of *Bacillus thuringiensis* by a foam flotation process in which added gelatin causes the spores to be selectively entrained in the foam and thereby separated from the suspensions.

3 Claims, No Drawings

4,247,644

FOAM FLOTATION PROCESS FOR SEPARATING *BACILLUS THURINGIENSIS* SPORULTION PRODUCTS

BACKGROUND OF THE INVENTION

1. Field of the Invention

The sporulating cells of *Bacillus thuringiensis* each produce a spore (endospore) and a diamond-shaped crystal (paraspore or inclusion body). At the completion of sporulation, the autolyzing cells release both of these bodies into the culture medium. The parasporal crystals are known to have insecticidal properties, and it is often desirable for investigative research and perhaps certain commercial purposes that these crystals be recovered in a substantially 100% pure state. However, it is difficult to separate the crystals from the spores because of similarity in their size and density. This invention relates to the removal of the interfering spores from a sporulated culture of *B. thuringiensis* in the course of isolating a pure crystal fraction.

2. Description of the Prior Art

Early techniques took advantage of the relative hydrophobicity of the spores as compared to the paraspores and isolated one from the other by phase separation. In the procedure described by T. A. Angus [J. Insect. Path. 1: 97–98 (1959)], the harvested bacterial culture was centrifuged repeatedly to remove the vegetative debris, and then stored for 7 days in a water suspension to germinate most of the spores. After four successive phase separations with a fluorocarbon, a crystal fraction of 95% purity was obtained. J. B. Bateson [Nature 205: 622–623 (1965)] was able to eliminate the need for germination and obtained crystals of 99% purity with only two successive fluorocarbon phase separations. However, the crystal yield was only about 3% and because of the high cost of the fluorocarbons, the procedure was not promising on a large scale. I. R. Pendleton et al. [Nature 212: 728–729 (1966)] found that an inexpensive solvent, carbon tetrachloride, could be substituted for the fluorocarbon if 75% of the spores were first removed by repeated flotation steps. These were conducted by shaking the sporulated suspension until a froth formed on the surface, selectively entrapping a portion of the spores. The subsequent phase separation gave crystal purities of 98–99%, but the average yield was only 35%. R. E. Gingrich [J. Invertebr. Path. 10: 180–184 (1968)] improved somewhat upon the procedure of Pendleton by sparging a centrifuge supernatant with air bubbles in a column. The spore-laden bubbles were continuously removed, leaving the crystal-enriched tailings. While this process had certain potential for large-scale separation, it proved to be time-consuming and recovered only about 76% of the paraspores.

More recent methods of isolating crystals have included isopycnic centrifugation in gradients of cesium chloride [P. G. Fast, J. Invertebr. Path. 20: 139–140 (1972)], centrifugation in linear gradients of Renografin [E. S. Sharpe et al., Appl. Environ. Microbiol. 30: 1052–1053 (1975)], and centrifugation in discontinuous gradients of Renografin [R. Milne et al., J. Invertebr. Path. 29: 230–231 (1977)]. By these techniques, the vegetative cells and cellular debris are easily removed because of their low buoyant densities ranging from about 1.02 to 1.12 g./cm.$^3$. However, separation of the crystals from spores is not readily achieved due to the proximity of their respective buoyant densities, approximately 1.25 and 1.30 g./cm.$^3$. Overloading the gradient results in overlapping of the bands. This problem, together with the tendency of the hydrophobic spores to clump and entrap crystals, limits both the amount of mixture which can be separated at one time as well as the purity of the fractions.

SUMMARY OF THE INVENTION

We have now discovered a rapid and efficient method for separating the spores from the parasporal crystals as part of a procedure for recovering pure crystals from a sporulated culture of *B. thuringiensis*. We have unexpectedly found that when a suspension containing both spores and crystals is subjected to foam flotation in the presence of added gelatin, substantially all of the crystals remain in the crystal-enriched suspension, and after a succession of foam flotations, an unprecedented percentage of the original number of spores are removed.

In accordance with this discovery, it is an object of the invention to prepare crystal-enriched suspensions of *B. thuringiensis* sporulation products.

It is also an object of the invention to remove at least 90% of the original spore count from suspension of the sporulation products.

Another object of the invention is to substantially reduce the time and effort necessary to recover a pure crystal fraction from a *B. thuringiensis* culture.

Other objects and advantages of this invention will become readily apparent from the ensuing description.

DETAILED DESCRIPTION OF THE INVENTION

This invention applies to treatment of suspensions prepared from cultures of *Bacillus thuringiensis* in which the sporulated cells have undergone autolysis and have released into the culture media the characteristic spores and crystals. It is contemplated that cultures containing the sporulation products of virtually any of the varieties of *B. thuringiensis* having crystalline paraspore can be treated by the disclosed process. Suitable culture media and growth conditions are well established in the art, and do not constitute a part of the invention. A suspension is normally prepared by scraping or otherwise recovering the bacterium colonies from the medium and dispersing them in an ample amount of water. Of course, the resultant dispersions may be further modified by dilution, filtration, or other routine type of treatment.

The objects of the invention are accomplished by adding to the suspension an amount of gelatin sufficient to cause the formation of a stable foam and promote the selective removal of spores at each stage of a multistage foam flotation. The actual quantity of gelatin required to be present in the suspension at the start of each stage of spore separation should be in the range of about 0.01% (w/v) to about 0.5% (w/v), wherein the percentage represents grams of gelatin per 100 ml. of suspension. It is noted that incompletely sporulated cultures have lower pH's and do not require the addition of as much gelatin as the completely sporulated cultures. Preferably gelatin is added prior to each stage of the foam flotation. It if is desired to add it less frequently, such as prior to every other stage, amounts near the upper end of the range will insure carryover to the next stage.

Any conventional agitation technique is suitable for promoting production of the foam. We have found that sonication and vigorous shaking in a closed vessel are the two methods which produce the best foams for selectively entraining the spores from the gelatin-containing suspensions, although sonication appears to more effectively dispel clumping. Sparging with a gas in a standing column and stirring in a blender are also viable alternatives. The agitation is continued until foam formation ceases. Depending on the particular method used, this period will generally range from about 0.25 to about 10 minutes. The temperature during flotation is not especially critical and room temperature will suffice.

After the agitation, the foam is allowed to drain for a few minutes before removing it by either suction or filtration. Light washing with water releases any entrapped crystals which may then be recombined with the crystal-enriched dispersion. The process is repeated three to five times or until only about 5-10% of the spores remain. At this point, a noticeable number of crystals began to appear in the foam. While this procedure has been described in terms of a batch operation, it is anticipated that the bubbles can be continuously removed from the surface of the suspension during agitation, and gelatin added as necessary.

The removed spores are substantially free of crystals and may be recovered from the foam by the addition of a small amount of antifoam agent and detergent, and then isolated by any known technique. Besides vegetative cells and debris, the crystal-enriched suspension typically contains over 90% of the original crystal count, and only 5-10% of the spores. Some of the spores and crystals are lost by adherence to the surface of the separation equipment, but 99% of the total crystal count recovered is found in the crystal-enriched suspension. On a laboratory scale, the preferred method of crystal recovery is gradient centrifugation. With 90-95% of the spores already removed, the capacity of the gradient is substantially increased, and the problem of overloading with the resultant overlap of the crystal and spore bands is minimized. The resultant crystal purity exceeds 99.9%, rendering them suitable for all anticipated purposes. Crystal recovery based upon the count applied to the gradient is on the order of 95%. Of course, it is understood that the crystals could be isolated from the enriched suspension by other conventional procedures such as phase separation. Another alternative would be to wash out the gelatin, germinate the spores, and remove the autolysis products of the resultant vegetative cells by repeated low-speed centrifugation.

The following examples are intended only to further illustrate the invention and are not intended to limit the scope of the invention which is defined by the claims.

EXAMPLE 1

B. thuringiensis HD-1 was grown on the following medium at 28° C. until sporulation and autolysis were complete (4-5 days):

| | |
|---|---|
| agar | 2.0 g. |
| yeast extract | 1.5 g. |
| glucose | 0.2 g. |
| $K_2HPO_4$ | 0.3 g. |
| water sufficient to make | 100 ml. |

After cultivation, the spores, crystals, and unsporulated cells were scraped off the medium and suspended in 200 ml. of distilled water by sonic vibration. A microscopic count indicated that this starting suspension contained $9 \times 10^{11}$ spores and $1.5 \times 10^{12}$ crystals. Gelatin [1 ml. of 2.5% (w/v)] in sterilized water solution was added to the culture suspension, and the mixture was shaken vigorously with the result that a foam formed on the suspension surface. After standing for about 2 minutes to permit draining, the foam was filtered through a glass wool plug in a large funnel and washed lightly with 1-2 ml. of distilled water. An additional 1 ml. of 2.5% gelatin solution was added to the filtrate and the above procedure was repeated using the same glass wool filter. The foam flotation process was then repeated three more times using a different glass plug for filtration. Microscopic counts gave the following percentages of the starting spore count removed with each of the five foam fractions:

| Foam fraction | Spores removed (%) |
|---|---|
| 1 | 46 |
| 2 | 21 |
| 3 | 13 |
| 4 | 8 |
| 5 | 5 |
| Total | 93 |

Crystals began to appear in the foam after five flotations. Fractions 1 through 5 were combined and washed with 0.1% detergent (Triton X) solution and traces of antifoam agent to break the foam. The combined spore fraction and the liquid filtrate (crystal-enriched suspension) were then diluted to 100 ml. and 500 ml., respectively, with water and subjected to microscopic counts. The results are shown in Table I.

EXAMPLE 2

A 290-mg. portion of the crystal-enriched fraction (Fraction C) obtained in Example 1 and containing $7.1 \times 10^{11}$ crystals was separated by linear gradient centrifugation using Renografin at 11,000 g. for 2 hours. Recovery of crystals applied to the gradient was 85% by dry weight (245 mg.) and 95% ($6.7 \times 10^{11}$) by microscopic count. The percentage of contaminant spores was 0.0006.

It is understood that the foregoing detailed description is given merely by way of illustration and that modification and variations may be made therein without departing from the spirit and scope of the invention.

TABLE I

| | Suspension | Crystals | Spores |
|---|---|---|---|
| A. | Original culture suspension | $1.5 \times 10^{12}$ | $9 \times 10^{11}$ |
| B. | Combined foam fraction | $1 \times 10^{10}$ | $8 \times 10^{11}$ |
| C. | Crystal-enriched fraction | $1.4 \times 10^{12}$ | $6 \times 10^{10}$ |
| D. | Total recovered (B + C) | $1.41 \times 10^{12}$ | $8.6 \times 10^{11}$ |
| E. | Percentage recovered (D/A) | 94% | 96% |
| F. | Foam fraction extraction efficiency (B/D) | 0.7% | 93% |
| G. | Crystal fraction extraction efficiency (C/D) | 99.3% | 7% |

We claim:

1. In a method for purifying parasporal crystals from a sporulated culture of *Bacillus thuringiensis*, wherein said method comprises removing spores by foam flotation from a suspension containing both said spores and said crystals, the improvement comprising:
a. adding gelatin to said suspension in an amount which, upon agitation, is sufficient to cause the formation of a stable foam and promote the selective removal of spores from said suspension;
b. agitating said suspension in the presence of said gelatin, thereby producing a substantially crystal-free, spore-bearing foam and a crystal-enriched suspension;
c. separating said foam from said crystal-enriched suspension; and
d. recovering said crystal-enriched suspension.

2. The method as described in claim 1 wherein said gelatin is added to said suspension at a level in the range of 0.01% to 0.5% (w/v).

3. The method as described in claim 1 wherein said crystal-enriched suspension separated in step (c) is recycled through steps (a) through (c) until at least 90% of the spores which were in the starting suspension have been removed.

* * * * *